US011078151B2

(12) United States Patent
Colbert et al.

(10) Patent No.: US 11,078,151 B2
(45) Date of Patent: Aug. 3, 2021

(54) PROCESS FOR THE PREPARATION OF STABLE TOLUENE DIAMINE RESIDUE/WATER BLENDS, RELATED COMPOSITIONS, AND METHODS OF USING SUCH BLENDS AS A FUEL

(71) Applicant: COVESTRO LLC, Pittsburgh, PA (US)

(72) Inventors: James William Colbert, Friendswood, TX (US); Mamadou Yaya Barry, Seabrook, TX (US); Jeremy Garrett, Baytown, TX (US); Ravindra S. Kamath, Pearland, TX (US)

(73) Assignee: Covestro LLC, Pittsburgh, PA (US)

( * ) Notice: Subject to any disclaimer, the term of this patent is extended or adjusted under 35 U.S.C. 154(b) by 226 days.

(21) Appl. No.: 16/478,181

(22) PCT Filed: Jan. 24, 2018

(86) PCT No.: PCT/US2018/014996
§ 371 (c)(1),
(2) Date: Jul. 16, 2019

(87) PCT Pub. No.: WO2018/140461
PCT Pub. Date: Aug. 2, 2018

(65) Prior Publication Data
US 2019/0367442 A1  Dec. 5, 2019

Related U.S. Application Data

(60) Provisional application No. 62/451,250, filed on Jan. 27, 2017.

(51) Int. Cl.
*C07C 209/90* (2006.01)
*C10L 1/32* (2006.01)
(Continued)

(52) U.S. Cl.
CPC ............ *C07C 209/90* (2013.01); *C10L 1/328* (2013.01); *F23G 5/02* (2013.01); *F23G 7/04* (2013.01);
(Continued)

(58) Field of Classification Search
CPC ... C07C 211/50; C07C 209/36; C07C 209/90; C10L 1/328; C10L 2200/0259;
(Continued)

(56) References Cited

U.S. PATENT DOCUMENTS

| 3,445,516 A | 5/1969 | Cross |
| 4,506,040 A * | 3/1985 | Raes ................. C08G 18/0871 252/182.27 |

(Continued)

FOREIGN PATENT DOCUMENTS

| CA | 2142911 A1 | 3/1994 |
| CN | 103896780 A | 7/2014 |
| CN | 104058973 A | 9/2014 |

OTHER PUBLICATIONS

International Search Report—PCT/US2018/014996; dated Apr. 24, 2018; authorized officer: Stefania Tabanella.

*Primary Examiner* — Ellen M McAvoy
*Assistant Examiner* — Chantel L Graham
(74) *Attorney, Agent, or Firm* — Donald R. Palladino (57) ABSTRACT

Processes for stabilizing toluenediamine residues are disclosed. These processes include adding a low viscosity, low boiling liquid to a toluenediamine residue composition to form a blend, and optionally, continuously monitoring the viscosity of the blend during addition of the low viscosity, low boiling liquid. The low viscosity, low boiling liquid may be added at 5% to 30% by weight based on the total weight of the blend. Further, the low viscosity, low boiling liquid may be added so that the blend has a viscosity of 10,000 cP (Continued)

or less throughout the temperature range of 40° C. to 95° C. Blends of toluenediamine residue compositions and low viscosity, low boiling liquids such as water, and methods of their use as a fuel are also disclosed.

21 Claims, 5 Drawing Sheets

(51) Int. Cl.
*F23G 5/02* (2006.01)
*F23G 7/04* (2006.01)

(52) U.S. Cl.
CPC . *C10L 2200/0259* (2013.01); *C10L 2290/141* (2013.01); *C10L 2290/24* (2013.01)

(58) Field of Classification Search
CPC .. C10L 2290/141; C10L 2290/24; F23G 5/02; F23G 7/04
See application file for complete search history.

(56) References Cited

U.S. PATENT DOCUMENTS

| | | |
|---|---|---|
| 5,449,832 A | 9/1995 | Van Court Carr et al. |
| 5,693,862 A | 12/1997 | Keyvani et al. |
| 5,714,634 A | 2/1998 | Casale et al. |
| 5,728,880 A * | 3/1998 | Beckhaus ............. C07C 209/84 203/71 |
| 5,849,947 A | 12/1998 | Biskup et al. |
| 6,004,482 A | 12/1999 | Adkins et al. |
| 6,472,564 B1 * | 10/2002 | Biskup ................. C07C 263/10 564/422 |
| 6,547,933 B2 | 4/2003 | Marion et al. |
| 6,673,960 B1 | 1/2004 | Schwarz et al. |
| 8,524,047 B2 | 9/2013 | Ogawa et al. |
| 9,365,503 B2 | 6/2016 | Biskup et al. |
| 2013/0130345 A1* | 5/2013 | Thai .......................... C07C 4/06 435/166 |

* cited by examiner

PROCESS FOR THE PREPARATION OF STABLE TOLUENE DIAMINE RESIDUE/WATER BLENDS, RELATED COMPOSITIONS, AND METHODS OF USING SUCH BLENDS AS A FUEL

CROSS-REFERENCE TO RELATED APPLICATION

This application is a national stage application under 35 U.S.C. § 371 of PCT/US2018/014996, filed Jan. 24, 2018, which claims the benefit of U.S. Provisional Application No. 62/451,250, filed Jan. 27, 2017, both of which are incorporated herein by reference.

FIELD

This invention pertains generally to processes for stabilizing toluenediamine (TDA) residues so they remain liquid at temperatures below the freezing point of the TDA residues. More specifically, the invention pertains to processes of stabilizing TDA residues by forming blends with low viscosity, low boiling liquids, such as water, to compositions comprising the blends, and to methods of using the blends as a fuel.

BACKGROUND

Isocyanates are prepared in large amounts and serve as starting materials for the preparation of polyurethanes, a widely used polymer. One of the most commonly used isocyanates is toluene diisocyanate (TDI), which is generally prepared by phosgenation of meta-toluenediamine (m-TDA). During phosgenation, however, contaminants of the m-TDA which were generated during its synthesis may clog equipment due to their high freezing or solidification point, and/or may affect production of the TDI.

These contaminants, also referred to as TDA residues, are therefore typically separated from the m-TDA by distillation and disposed of by incineration. Because of their high freezing or solidification point, the TDA residues need to be stored at elevated temperatures (e.g., >100° C.) to ensure that they remain liquid prior to disposal. Thus, it would be desirable to stabilize the TDA residues so that they may be stored at lower temperatures. Further, it would be desirable to find a greener and more cost effective method for disposal of the TDA residues.

SUMMARY

These and other benefits are accomplished by the processes, methods, and compositions of the present invention. Thus, the present invention provides processes for stabilizing toluenediamine residues that comprise adding a low viscosity, low boiling liquid to a toluenediamine residue composition to form a blend, wherein the blend comprises 5 to 30% by weight of the low viscosity, low boiling liquid, based on the total weight of the blend, and has a viscosity of 10,000 cP (10,000 mPa·s) or less throughout a temperature range of 40° C. to 95° C.

The present invention also provides blended compositions comprising: 70 to 95% by weight of a toluenediamine residue composition, and 5 to 30% by weight of a low viscosity, low boiling liquid, based on the total weight of the blended composition, wherein the blended composition has a viscosity of 10,000 cP (10,000 mPa·s) or less throughout a temperature range of 40° C. to 95° C.

The present invention further provides methods of use of a toluenediamine residue composition as a fuel, wherein the method comprises adding 5 to 30% by weight of a low viscosity, low boiling liquid to the toluenediamine residue composition to form a fuel blend, wherein the weight percents are based on the total weight of the fuel blend, and wherein the fuel blend has a viscosity of 10,000 cP (10,000 mPa·s) or less throughout a temperature range of 40° C. to 95° C., and has a heat content, i.e., heat of combustion, of at least 10,000 BTU/lb (23,260 kJ/kg).

The present invention further provides methods of using a toluenediamine residue composition as a fuel. These methods comprise: (a) feeding a blend comprising the toluenediamine residue composition to a fuel burning apparatus, wherein the blend comprises 70 to 95% by weight of the toluenediamine residue composition and 5 to 30% by weight of a low viscosity, low boiling liquid, wherein the weight percents are based on the total weight of the blend; and (b) burning the blend in the fuel burning apparatus, wherein the blend has a viscosity of 10,000 cP or less throughout the temperature range of 40° C. to 95° C.

DETAILED DESCRIPTION

Various embodiments of the present invention include processes for stabilizing toluenediamine ("TDA") residues by reducing the solidification or freezing point of a composition comprising the TDA residues. Thus, provided herein is a process for stabilizing TDA residues by forming blends with low viscosity, low boiling liquids such as water so that the blends remain liquid (e.g., have a viscosity of 10,000 cP (10,000 mPa·s) or less) at temperatures as low as 50° C., or as low as 40° C., or even 20° C. The blends may remain liquid (e.g., have a viscosity of 10,000 cP or less) at all temperatures throughout the range of 50° C. to 95° C., such as 40° C. to 95° C., or even 20° C. to 95° C. These blends may then be stored and/or shipped at these relatively low temperatures for further processing, including, in some embodiments, for use as a liquid fuel. Other embodiments of the present invention are directed to methods of use of TDA residues as a fuel, to compositions comprising blends of TDA residues and a low viscosity, low boiling liquid, and to compositions and fuels formed by the processes and methods disclosed herein.

It is to be understood that certain descriptions of the disclosed embodiments have been simplified to illustrate only those steps, elements, features, and aspects that are relevant to a clear understanding of the disclosed embodiments, while eliminating, for purposes of clarity, other steps, elements, features, and aspects. Persons having ordinary skill in the art, upon considering the present description of the disclosed embodiments, will recognize that other steps, elements, and/or features may be desirable in a particular implementation or application of the disclosed embodiments. However, because such other steps, elements, and/or features may be readily ascertained by persons having ordinary skill upon considering the present description of the disclosed embodiments, and are not necessary for a complete understanding of the disclosed embodiments, a description of such steps, elements, and/or features is not provided herein. As such, it is to be understood that the description set forth herein is merely exemplary and illustrative of the disclosed embodiments and is not intended to limit the scope of the invention as defined solely by the claims.

Throughout this description and in the appended claims, use of the singular includes the plural and plural encompasses singular, unless specifically stated otherwise. For example, although reference is made herein to "an" isomer, "a" composition, "a" fuel, and "a" blend, one or more of any of these components and/or any other components described herein can be used.

Unless otherwise indicated, all numerical parameters are to be understood as being prefaced and modified in all instances by the term "about", in which the numerical parameters possess the inherent variability characteristic of the underlying measurement techniques used to determine the numerical value of the parameter. At the very least, and not as an attempt to limit the application of the doctrine of equivalents to the scope of the claims, each numerical parameter described in the present description should at least be construed in light of the number of reported significant digits and by applying ordinary rounding techniques.

The term "viscosity", as used herein, refers to the dynamic viscosity, which is the quantitative expression of a fluid's resistance to flow or shear when the fluid is in motion. That is, dynamic (absolute) viscosity is the tangential force per unit area required to move one horizontal plane with respect to another plane—at a unit velocity—when maintaining a unit distance apart in the fluid. Thus, dynamic viscosity is generally measured using the damping effect that a fluid has on the motion of a measurement object, such as a resonating tube or pendulum, and is expressed in units of mPa·s (SI units) or cP (centipoise). In general, dynamic viscosity of fluids is little affected by the pressure at which the measurement is taken, but as reported herein, viscosity measurements are taken and reported at atmospheric pressure. The viscosity values reported herein can be determined using a dynamic viscometer, such as a Brookfield viscometer (DV-I™ Viscometer from Brookfield Engineering, with spindle #18 or #31 at 100 rpm) or with a Coriolis mass flowmeter (such as the Proline Promass from Endress+ Hauser) that measures the force resulting from the acceleration caused by mass moving toward (or away from) a center of rotation. The straight single-tube design of the Proline Promass flowmeter provides the regular Coriolis flowmeter outputs of mass flow, density and temperature, additionally it provides in-line viscosity measurement as an optional output values.

Also, any numerical range recited herein is intended to include all sub-ranges subsumed therein. For example, a range of "1 to 10" is intended to include all sub-ranges between (and including) the recited minimum value of 1 and the recited maximum value of 10, that is, having a minimum value equal to or greater than 1 and a maximum value equal to or less than 10. Any maximum numerical limitation recited herein is intended to include all lower numerical limitations subsumed therein and any minimum numerical limitation recited herein is intended to include all higher numerical limitations subsumed therein. Accordingly, applicant(s) reserves the right to amend the present disclosure, including the claims, to expressly recite any sub-range subsumed within the ranges expressly recited herein. All such ranges are intended to be inherently disclosed herein such that amending to expressly recite any such sub-ranges would comply with the requirements of 35 U.S.C. § 112 and 35 U.S.C. § 132(a).

TDA residues are a byproduct formed during synthesis of toluenediamine. It is known that aromatic diamines, such as TDA, can be prepared by nitration of an aromatic compound to form an aromatic dinitro compound, followed by catalytic hydrogenation of the aromatic dinitro compound to form the aromatic amine. The hydrogenation can be carried out with solvents, such as methanol, ethanol or isopropanol or without such solvents. The hydrogenation can be carried out with the aid of catalysts dispersed in the reaction mixture. Doped or non-doped Raney nickel catalysts and/or metal catalysts, which contain, for example, iridium, cobalt, copper, palladium, or platinum can be used as the catalyst.

In addition to the aromatic diamine and a water co-product, organic by-products are also formed during the hydrogenation step. These organic by-products are conventionally divided into low-boiling substances and high-boiling substances based on their boiling point relative to the aromatic diamine, or into various groups according to their chemical characteristics.

Thus, in the case of industrial nitration of toluene to give dinitrotoluene (DNT) and hydrogenation thereof to give TDA, a crude TDA mixture is formed which, in addition to water and isomers of TDA, contains several such organic by-products. The non-aqueous content of the crude TDA mixture can include meta-TDA isomers (m-TDA; 2,4- and 2,6-TDA), ortho-TDA isomers (o-TDA; 2,3- and 3,4-TDA), and para-TDA isomer (p-TDA; 2,5-TDA), and generally 3 to 5% by weight of low-boiling substances and 0.2 to 2% by weight of high-boiling substances based on the total weight of the non-aqueous content of the crude TDA mixture.

Low-boiling substances as referred to in the context of this invention are compounds which have a lower boiling point than the 2,4-TDA isomer, and high-boiling substances are those compounds which have a higher boiling point than the 2,6-TDA isomer (the boiling points being 283° C. and 289° C. for 2,4- and 2,6-TDA, respectively, measured at atmospheric pressure). Examples of low-boiling substances include toluidines and ammonia. Examples of high boiling substances include oligomeric species formed by oxidative coupling of two TDA isomers such as diphenylmethanes, diphenylamines, acridines and phenazines.

The high boiling substances are generally referred to as TDA residues. Thus, in the context of the present invention, the term "TDA residue" may include collectively the organic compounds formed during TDA synthesis that have a boiling point greater than the 2,6-TDA isomer. The term TDA residue also includes certain organic compounds which contain at least two aromatic rings. Additionally, the TDA residue may include a mixture of the organic compounds mentioned with residues of the catalyst, i.e., heavy metals, such as iridium, copper, cobalt, nickel, iron, palladium and/or platinum.

The crude TDA mixture thus obtained by the hydrogenation reaction is conventionally purified to separate the m-TDA and o-TDA isomers, and to remove the low and high boiling substances. This purification can be carried out by distillation, crystallization and/or after-treatment with heat as well as chemical oxidation or reduction processes.

In large-scale industrial processes, the purification process is often carried out by distillation, and, in this way, the water of reaction and low-boiling substances, such as toluidines and ammonia, and optionally solvents (e.g., methanol, ethanol, propanol), are partly or completely removed. Separation of the water, the low-boiling substances, and optionally the solvents, can then be carried out in one or more additional stages. Removal of one or more of the o-TDA isomers may be carried out in an additional distillation column. The m-TDA isomer, and the high boiling substances (i.e., TDA residue) remain after this additional distillation step.

While the amount of TDA residue which remains in this final step is relatively small (i.e., approximately 2% by weight based on the total weight of the feed), its separation from the m-TDA is important for isocyanate production. TDA residues form higher molecular weight compounds during reaction of the m-TDA with phosgene to give the diisocyanate. These higher molecular weight compounds often have relatively high solidification or freezing temperatures, and/or very high viscosities, and may clog the equipment used to produce the isocyanate. Thus, removal of the TDA residues not only leads to a higher purity isocyanate, but also more efficient isocyanate production from the m-TDA.

The TDA residue can be separated from the m-TDA isomer in a distillation column, wherein essentially pure m-TDA is separated in the top phase and the TDA residue is concentrated in the bottom phase until the high boiling substance content is from approximately 25 to 60% by weight, based on the total weight of the TDA residue and the m-TDA isomer in the composition. That is, distillation may be stopped at a point where a certain amount of the m-TDA isomer remains so that the high boiling substances, which are very viscous, may be maintained within a workable viscosity range.

As such, the term "toluenediamine residue composition" as described herein refers to a composition comprising 25 to 60% by weight of TDA residue and 40 to 75% by weight of m-TDA isomer, based on the total weight of the TDA residue and the m-TDA isomer in the composition. According to certain aspects of the present invention, the toluenediamine residue composition as described herein refers to a composition comprising 40 to 60% by weight of TDA residue and 40 to 60% by weight of m-TDA isomer, or even 50% by weight TDA residue and 50% by weight m-TDA isomer, based on the total weight of the TDA residue and the m-TDA isomer in the composition.

The m-TDA isomer component of the toluenediamine residue composition can be exchanged with the aid of auxiliary substances foreign to the composition, or auxiliary substances from prior steps in the purification process. One exemplary auxiliary substance includes the TDA isomer mixture isolated as part of the first distillation step (o-TDA/m-TDA/high boiling substances mixture from the bottom of the column) or the o-TDA isomer isolated as part of the subsequent distillation step (o-TDA from the top of the column) For example, the toluenediamine residue composition comprising mainly m-TDA and TDA residue can be mixed with an o-TDA isomer in a weight/weight (w/w) ratio of 5:1 to 1:5, such as 1:1 to 1:5 (i.e., ratio of weight of m-TDA and TDA residue to weight of o-TDA). The resulting m-TDA/o-TDA mixture can then be recovered from the composition (which includes the TDA residue) by further distillation. In this way, the amount of m-TDA in the bottom phase (toluenediamine residue composition) can be reduced and/or exchanged with o-TDA isomer.

Thus, toluenediamine residue compositions as described herein refers to a composition comprising 25 to 60% by weight of TDA residue and 40 to 75% by weight of o-TDA isomer, based on the total weight of the TDA residue and the o-TDA isomer in the composition. According to certain aspects of the present invention, the toluenediamine residue composition as described herein refers to a composition comprising 40 to 60% by weight TDA residue and 40 to 60% by weight o-TDA isomer, or even 50% by weight TDA residue and 50% by weight o-TDA isomer, based on the total weight of the TDA residue and the o-TDA isomer in the composition.

The toluenediamine residue composition in this bottom phase may also comprise a mixture of the o-TDA and m-TDA isomers. Thus, the toluenediamine residue composition can comprise 25 to 60% by weight of TDA residue and 40 to 75% by weight m-TDA/o-TDA isomer mixture, such as 40 to 60% by weight TDA residue and 40 to 60% by weight m-TDA/o-TDA isomer mixture, or even 50% by weight TDA residue and 50% by weight m-TDA/o-TDA isomer mixture, based on the total weight of the TDA residue and the m-TDA/o-TDA isomer mixture in the composition, and wherein the ratio of m-TDA to o-TDA isomer in the toluenediamine residue composition may be a w/w ratio of 5:1 to 1:5, such as 4:1 to 1:4, or even 2:1 to 1:2. According to certain aspects of the present invention, the w/w ratio of m-TDA to o-TDA isomer in the toluenediamine residue composition may be 1:4.

The toluenediamine residue composition as described herein has historically been stored in tanks maintained at temperatures above the solidification or freezing point of the material, typically above 100° C., such as between 100° C. and 145° C., to ensure it remains liquid for proper handling. Lower temperatures have been avoided because they lead to viscosity build-ups, blockages in process equipment, freezing and the subsequent need to reheat the material. The current prevalent method for disposal of the toluenediamine residue composition is incineration at facilities which are able to handle the composition at these elevated temperatures.

The present invention provides a process to reduce the solidification or freezing point of the toluenediamine residue composition by mixing the toluenediamine residue composition with a low viscosity, low boiling liquid. As used herein, a "low viscosity, low boiling liquid" means a liquid having a viscosity of 100 cP or less (100 mPa·s or less measured at 23° C.), and a boiling point of 210° C. or less (measured at atmospheric pressure). Exemplary low viscosity, low boiling liquids include water, the low boiling substances recovered during early stages of the crude TDA purification process, small organic compounds such as amines and aniline, and organic solvents including alcohols and low molecular weight hydrocarbons. As used herein, "low molecular weight" means compounds having a weight average molecular weight of 600 Daltons or less, such as 300

Daltons or less, or 150 Daltons or less. As used herein, the term "molecular weight", when used with reference to oligomers or polymers, refers to the weight average molecular weight Mw and can be determined by means of gel permeation chromatography (GPC) using small molecules or polystyrene samples of known molar mass for calibration.

As used herein, the terms "solidification point" and/or "freezing point" are used interchangeably, and means the temperature at which the transition from a liquid state to a solid state takes place (at atmospheric pressure). The solidification or freezing point of a specific toluenediamine residue composition may vary, and is dependent on at least the % by weight of the TDA residue in the toluenediamine residue composition.

Thus, the process to reduce the solidification or freezing point of the toluenediamine residue composition may include mixing "hot" toluenediamine residue composition, where the composition is at a temperature just below 100° C., or greater than 100° C., such as greater than 145° C., or even 145° C. to 200° C., with a low viscosity, low boiling liquid. The temperature of the toluenediamine residue composition when it is mixed with the low viscosity, low boiling liquid may depend on the identity of the low viscosity, low boiling liquid. For example, if the low viscosity, low boiling liquid is water, the toluenediamine residue composition may be cooled to a temperature of just below 100° C. to prevent flashing. It is also possible to supply each component at pressures greater than ambient, and as such, the temperature at which the toluenediamine residue composition and low viscosity, low boiling liquid are supplied may further depend on the pressure.

The low viscosity, low boiling liquid may be added in an amount of 5 to 30% by weight, such as 10 to 25% by weight, or 10 to 20% by weight, or even 15 to 20% by weight, based on the total weight of the resulting blend comprising the toluenediamine residue composition and the low viscosity, low boiling liquid. The low viscosity, low boiling liquid may be added at any temperature, such as 20° C. or greater, or even 40° C. or greater. The blend may be cooled by action of the low viscosity, low boiling liquid addition, by an external cooling system, or a combination thereof. The blend may be cooled to a temperature of 95° C. or less, such as 50° C. or less, 45° C. or less, or even 41° C. or less.

According to certain embodiments of the process, the low viscosity, low boiling liquid may be water. Thus, the process may include mixing the toluenediamine residue composition with water to form a blend. The water may be added in an amount of 5 to 30% by weight, such as 10 to 25% by weight, or 10 to 20% by weight, or even 15 to 20% by weight, based on the total weight of the resulting blend comprising the toluenediamine residue composition and the water.

According to certain embodiments of the process, the low viscosity, low boiling liquid may be the low boiling substances which were purified at early stages of the TDA purification process. Thus, the process may include mixing the toluenediamine residue composition with these low boiling substances to form a blend. The low boiling substances may be added at 5 to 30% by weight, such as 10 to 25% by weight, or 10 to 20% by weight, or even 15 to 20% by weight, based on the total weight of the resulting blend comprising the toluenediamine residue composition and the low boiling substances.

Additionally, water may also be added to a blend comprising toluenediamine residue composition and low boiling substances which were purified at early stages of the TDA purification process. In certain embodiments, the water is added at 1 to 30% by weight, such as 5 to 15% by weight, or 5 to 10% by weight, based on the total weight of such resulting blends that further include the water. As above, the water may be added at any temperature, such as 20° C. or greater, or even 40° C. or greater. The blend may be cooled by action of the low boiling substances addition, the water addition, by an external cooling system, or a combination thereof. The blend may be cooled to a temperature of 95° C. or less, such as 50° C. or less, 45° C. or less, or even 41° C. or less. The blend may be cooled to a temperature of 20° C. to 95° C., such as 20° C. to 50° C., 20° C. to 45° C., or 20° C. to 41° C.

The water added in any of the above mixtures may be process water, such as the water recovered during early stages of the crude TDA mixture purification to isolate the m-TDA, as described above. For example, the process water may be the water recovered in the first distillation column in the purification process of the crude TDA mixture. Alternatively, or in addition, the water may be facility water, such as water that is supplied from an outside source, or from another process within the facility.

The process design and control provided by the present invention allows flexibility regarding the amount of low viscosity, low boiling liquid added to form the blend, and the final temperature of the blend, both of which can be tuned as needed. For example, the viscosity and temperature of the blend may be selected based on knowledge of a storage, transport, or delivery viscosity and/or temperature for the blend, and/or on knowledge of the requirements for a final use of the blend (e.g., as a liquid fuel).

According to certain aspects of the present invention, the process may include continuous monitoring of the viscosity of the blend. As such, the amount of low viscosity, low boiling liquid (e.g., water, low boiling substance, solvent, etc.) added to the toluenediamine residue composition to form the blend may be tuned to a specific desired viscosity or viscosity range.

Furthermore, continuous monitoring of the viscosity may act as a failsafe for the process equipment, preventing process disruptions due to incorrect blend ratios. That is, continuous monitoring of the viscosity may provide an expected viscosity even when certain parts of the equipment may not function to specification. For example, an improper measurement of the toluenediamine residue composition flow may lead to an incorrect calculation for the amount of low viscosity, low boiling liquid to be added to form the blend having a specific viscosity, and/or to an incorrect blend ratio. Alternatively, improperly calibrated feed lines for the low viscosity, low boiling liquid could lead to addition amounts that are not correct. Continuous monitoring of the viscosity during addition of the low viscosity, low boiling liquid can provide real-time feedback of the actual amounts added, and allow the process equipment to automatically correct the addition amount, or a process engineer to manually correct the addition amount.

Thus, the present invention provides a process for stabilization of toluenediamine residues. The process comprises adding a low viscosity, low boiling liquid to a toluenediamine residue composition to form a blend, wherein the blend comprises 5 to 30% by weight of the low viscosity, low boiling liquid, based on the total weight of the blend, and the blend has a viscosity of 10,000 cP (10,000 mPa·s) or less throughout the temperature range of 50° C. to 95° C., or 40° C. to 95° C., or even 20° C. to 95° C. According to certain aspects of the present invention, the blend comprises 10 to 20% by weight of the low viscosity, low boiling liquid, based on the total weight of the blend. According to certain aspects of the present invention, the blend comprises 15 to 20% by weight of the low viscosity, low boiling liquid, based on the total weight of the blend. According to certain aspects of the present invention, the blend may have a viscosity of 4,000 cP (4,000 mPa·s) or less, such as 2,000 cP (2,000 mPa·s) or less, or even 1,000 cP (1,000 mPa·s) or less throughout the temperature range of 50° C. to 95° C., such as 40° C. to 95° C., or even 20° C. to 95° C.

According to certain aspects of the present invention, the process may include continuously monitoring a viscosity of the blend during addition of the low viscosity, low boiling liquid; and controlling, i.e., adjusting or varying, the addition amount of the toluenediamine residue composition and/or the addition amount of the low viscosity, low boiling liquid based on the monitored viscosity. For example, in a continuous process, the amount of toluenediamine residue composition and/or low viscosity, low boiling liquid may be adjusted based on the viscosity reading, while in a static system, addition of the toluenediamine residue composition and/or low viscosity, low boiling liquid may be stopped when the viscosity of the blend is equal to a desired viscosity. Moreover, according to certain aspects of the present invention, the blend is passed through a heat exchanger to bring the temperature of the blend to a target temperature range for its end use (such as use as a liquid fuel), such as, for example, a target temperature range of 20° C. to 95° C., 30° C. to 50° C., 35° C. to 45° C., or 38° C. to 42° C.

The present invention also provides blends of a toluenediamine residue composition and a low viscosity, low boiling liquid prepared according to any of the processes described herein.

The present invention further provides a blend comprising 70 to 95% by weight of the toluenediamine residue composition detailed herein, and 5 to 30% by weight of a low viscosity, low boiling liquid, based on the total weight of the blend. According to certain aspects of the present invention, the blend may comprise 80 to 90% by weight of the toluenediamine residue composition and 10 to 20% by weight of the low viscosity, low boiling liquid, based on the total weight of the blend. According to certain aspects of the present invention, the blend may comprise 85 to 90% by weight of the toluenediamine residue composition and 10 to 15% by weight of the low viscosity, low boiling liquid, based on the total weight of the blend.

According to certain aspects of the present invention, the various blends described herein may be used as a fuel in a fuel burning apparatus configured to utilize liquid fuels. These may include domestic, commercial and industrial apparatus. The fuel burning apparatus may be a boiler for commercial applications such as boilers for power plants or utility plants; an incinerator such as a rotary kiln incinerator, liquid injection kiln, fluidized bed kiln, cement kiln; and even steel and aluminum forging furnaces.

The present invention also provides methods of use of the toluenediamine residue composition as a liquid fuel in any of these energy intensive processes (e.g., cement kilns). This inventive method of use of the toluenediamine residue composition as a fuel would reduce the reliance on other fuels such as coal or natural gas, and would remove the material from the waste stream. Further, this transition from incineration to use as a fuel enables a reduction of primary energy consumption at the TDA production facilities.

TDA residue in its normal form, however, does not meet the requirements for use as a liquid fuel source due to the very high freezing or solidification temperature, typically 96° C. to 105° C. In cement kilns, for example, the toluenediamine residue composition would be mixed with a variety of organic wastes and raw materials before entering the kiln. Due to the changing nature of the feed mixtures, however, there are strict requirements the toluenediamine residue composition must fulfill to ensure that the safety and operational aspects of the cement kiln are not compromised.

Cement is the active ingredient in concrete, and is produced in huge rotary kilns by heating a mixture of minerals to over 1400° C. This is a very energy intensive process and cement manufacturers have developed technology that allows them to use energy-rich secondary materials created by other industrial processes to replace non-renewable fossil fuels. Such technology does have certain requirements such as, for example, the viscosity of the secondary materials and the temperature at which the secondary material is supplied. In general, a secondary material for use in a cement kiln needs to be supplied for input to the kiln at a viscosity of not more than 10,000 cP (10,000 mPa·s), such as not more than 4,000 cP (4,000 mPa·s), not more than 2,000 cP (2,000 mPa·s), or even not more than 1,000 cP (1,000 mPa·s). Additionally, the secondary material needs to be supplied for input to the kiln at a temperature of 95° C. or less, such as 50° C. or less, of 45° C. or less, or even 41° C. or less.

Thus, the present invention provides methods of using a toluenediamine residue composition as a fuel, wherein the method generally comprises adding 5 to 30% by weight of a low viscosity, low boiling liquid to the toluenediamine residue composition to form a fuel blend, wherein the weight percents are based on the total weight of the fuel blend, and wherein the fuel blend comprises a viscosity of 10,000 cP (10,000 mPa·s) or less at a temperature of 95° C. or less, such as throughout the temperature range of 50° C. to 95° C., or 40° C. to 95° C., or even 20° C. to 95° C. The fuel may have a heat content of at least 10,000 BTU/lb (23,260 kJ/kg).

In addition, some embodiments of the present invention are directed to methods of using a toluenediamine residue composition as a fuel, wherein the method generally comprises (i) feeding a blend comprising the toluenediamine residue composition to a fuel burning apparatus, wherein the blend comprises 70 to 95% by weight of a toluenediamine residue composition and 5 to 30% by weight of a low viscosity, low boiling liquid, wherein the weight percents are based on the total weight of the blend; and (ii) burning the blend in the fuel burning apparatus, wherein the blend has a viscosity of 10,000 cP (10,000 mPa·s) or less at a temperature of 95° C. or less, such as throughout the temperature range of 50° C. to 95° C., or 40° C. to 95° C., or even 20° C. to 95° C. The fuel may have a heat content of at least 10,000 BTU/lb (23,260 kJ/kg).

According to certain aspects of such methods, the viscosity may be 4,000 cP (4,000 mPa·s) or less, 2,000 cP (2,000 mPa·s) or less, or even 1,000 cP (1,000 mPa·s) or less at the temperature of 95° C. or less, 50° C. or less, 45° C. or less, or even 41° C. or less; such as throughout the temperature range of 50° C. to 95° C., or 40° C. to 95° C., or even 20° C. to 95° C. According to certain aspects of the method, 5 to 20% by weight of a low viscosity, low boiling liquid, or even 10 to 20% by weight of a low viscosity, low boiling liquid may be added to the toluenediamine residue composition to form a fuel blend, based on the total weight of the fuel blend. According to certain aspects of such methods, the toluenediamine residue composition generally comprises TDA residues, which includes compounds formed during TDA synthesis that have a higher boiling point than the 2,6-TDA isomer. The TDA isomers may comprise meta-toluenediamine (2,4-diamine toluene, 2,6-toluene diamine), ortho-toluenediamine (2,3-diamine toluene, 3,4-diamine toluene), or a combination thereof.

According to certain aspects of the method, the toluenediamine residue composition may find use as a fuel in a cement kiln.

Thus, the present invention also provides a fuel composition comprising 70 to 95% by weight of a toluenediamine residue composition and 5 to 30% by weight of a low viscosity, low boiling liquid, wherein the fuel has a viscosity of 10,000 cP (10,000 mPa·s) or less throughout the temperature range of 50° C. to 95° C., or 40° C. to 95° C., or even 20° C. to 95° C.

According to certain aspects of the present invention, the fuel may comprise 80 to 90% by weight of the toluenediamine residue composition detailed herein and 10 to 20% by weight water. According to certain aspects of the present invention, the fuel may comprise 85 to 90% by weight of the toluenediamine residue composition detailed herein and 10 to 15% by weight water. Further, the viscosity of the fuel may be 4,000 cP (4,000 mPa·s) or less throughout the temperature range of 50° C. to 95° C., or 40° C. to 95° C., or even 20° C. to 95° C. The viscosity of the fuel may be 2,000 cP (2,000 mPa·s) or less at throughout the temperature range of 50° C. to 95° C., or 40° C. to 95° C., or 20° C. to 95° C. The viscosity of the fuel may be 1,000 cP (1,000 mPa·s) or less throughout the temperature range of 50° C. to 95° C., or 40° C. to 95° C., or 20° C. to 95° C. Further, the viscosity of the fuel may be 4,000 cP (4,000 mPa·s) or less at a temperature of 50° C. or less, 2,000 cP (2,000 mPa·s) or less at a temperature of 50° C. or less, or even 1,000 cP (1,000 mPa·s) or less at a temperature of 50° C. or less.

According to certain aspects of the present invention, the fuel may have a heat content of at least 10,000 BTU/lb (23,260 kJ/kg), and may find use in a cement kiln.

Having thus described our invention, the following examples are given as being illustrative thereof. All parts and percentages given in these examples are parts by weight and percentages by weight, unless otherwise indicated.

EXAMPLES

Several schematic diagrams are provided which detail various embodiments of the process of the present invention. Further, several experiments have been conducted to measure the viscosity and phase stability of various blends, and to provide qualitative evaluations thereof.

Example 1

Figure 1:
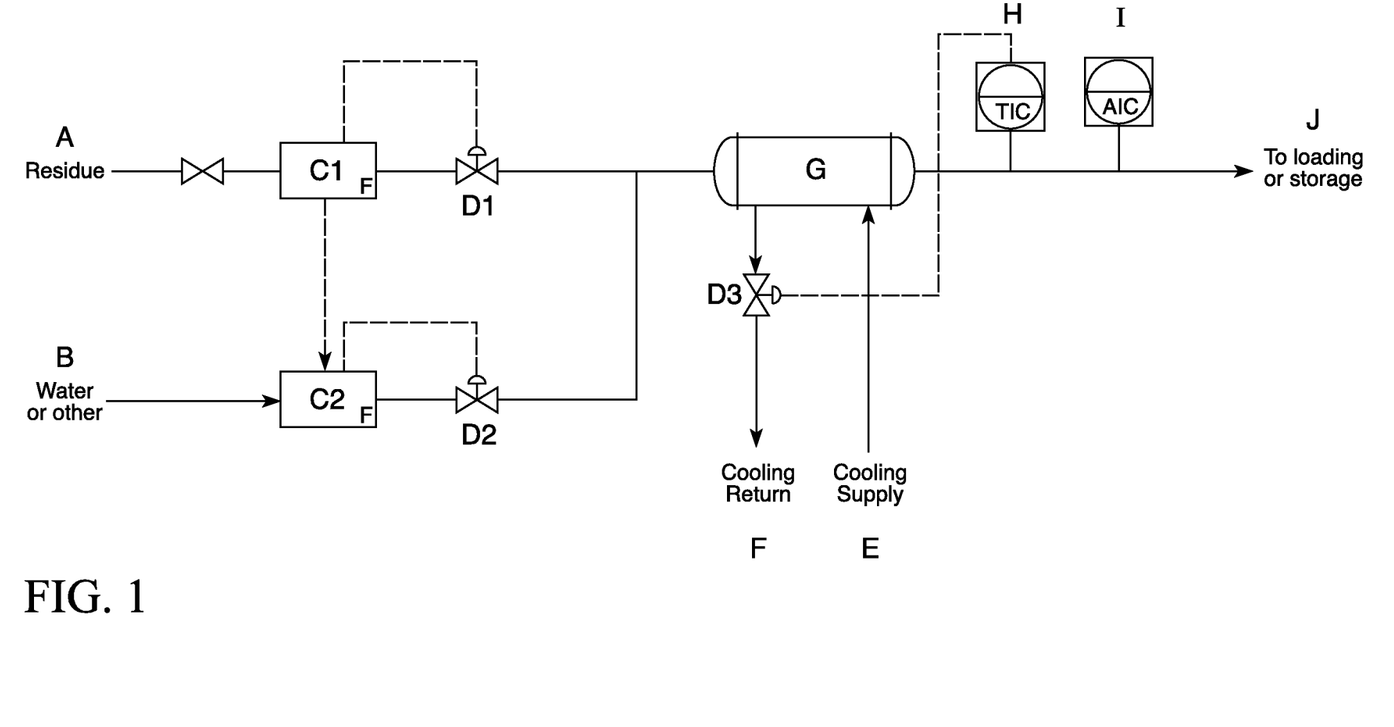
FIG. 1 is a schematic diagram illustrating process control for an embodiment of a process of stabilizing toluenediamine residue compositions according to the present invention.

Shown in FIG. 1 is a schematic diagram for an embodiment of a process control which may be used to practice the process of the present invention. More specifically, the control scheme shown in FIG. 1 consists of an input of a toluenediamine residue composition (A) and an input of water or another low viscosity, low boiling liquid (B). Flow control for A and B can be provided by valves on the feed lines (shown as pneumatic valves D1 and D2, respectively) which communicate with flowmeters (C1 and C2, respectively). This exemplary blending station continuously mixes toluenediamine residue composition (A) with water or the other low viscosity, low boiling liquid (B) in set proportions and cools the blend by heat exchanger G (using a cooling medium supplied from E and returned via F) to a desired temperature before storage or loading (J) for transfer.

Instrumentation and controls (e.g., meters C1 and C2, and valves D1 and D2) can ensure that all stream flows are metered and added in appropriate amounts to reach a target blend composition. For example, the control system may adjust the flow rate of B based on the flow rate of A and the desired concentration of B in the blend. The setup allows for the blend ratio to be changed in order to make blends of different compositions.

After the streams are mixed, the blend can be cooled to a specific desired temperature. The flow of the cooling medium may be adjusted (up or down using valve D3) to reach the desired temperature based on feedback from a temperature meter (TIC; H). A viscosity meter (AIC; I) can monitor the viscosity of the blend as a way to catch any deviations in the desired blend ratio (i.e., amounts of A and B added). Alternatively, feedback from the viscosity meter could be used to change the ratio of the components (i.e., A and B) provided to form the blend so that the blend stays within a specified viscosity range. In certain embodiments, the viscosity meter (I) may be a Coriolis mass flowmeter which measures mass flow, viscosity and other parameters.

Example 2

Figure 2:
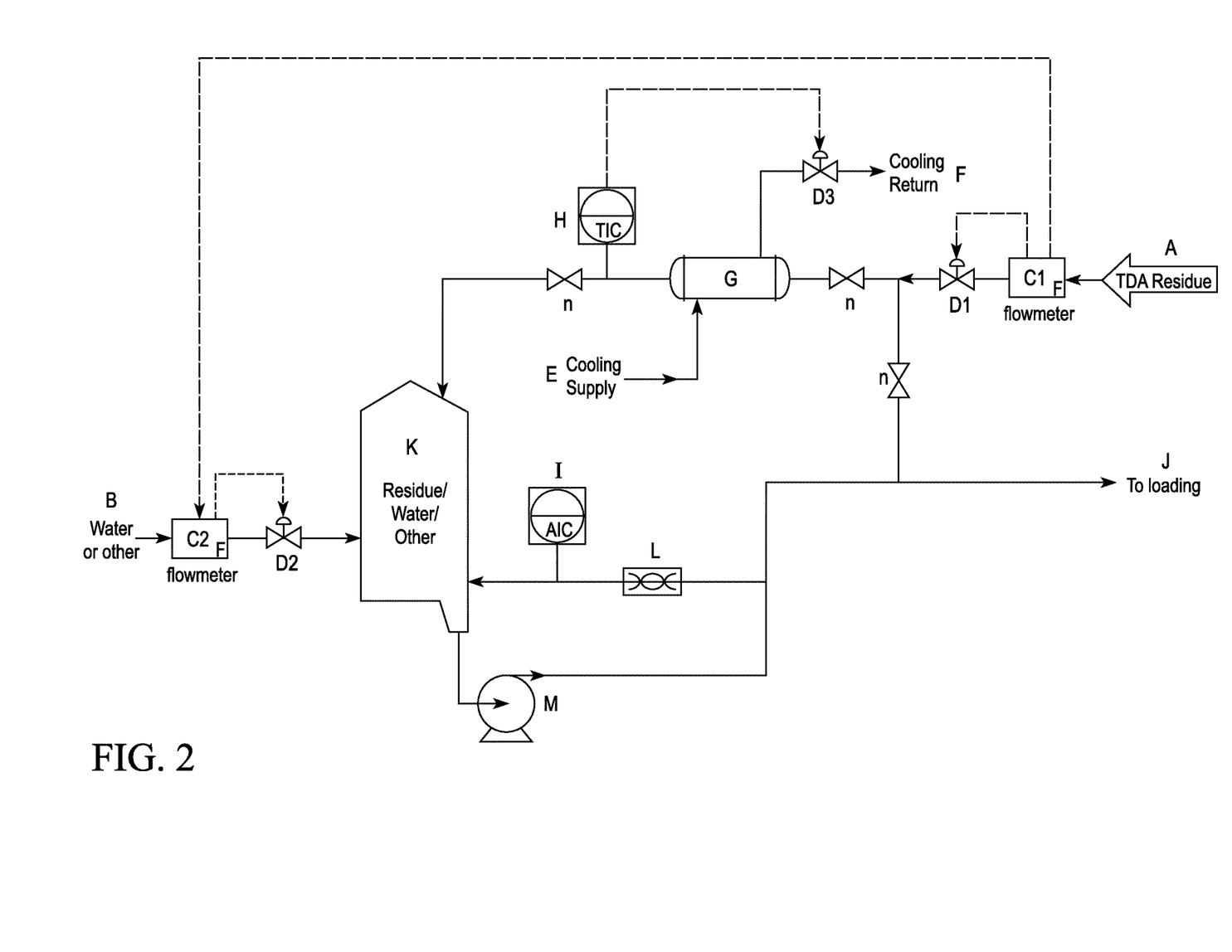
FIG. 2 is a schematic diagram illustrating another process control for an embodiment of a process of stabilizing toluenediamine residue compositions according to the present invention.

Shown in FIG. 2 is a schematic diagram for another embodiment of a process control which may be used to practice the process of the present invention. More specifically, the control scheme shown in FIG. 2 consists of an input of a toluenediamine residue composition (A) and an input of water or another low viscosity, low boiling liquid (B), both of which are directed to a tank (K). Flow control for A and B can be provided by valves on the feed lines (shown as pneumatic valves D1 and D2, respectively) which communicate with flowmeters (C1 and C2, respectively).

In this exemplary process control, the toluenediamine residue composition (A) may be cooled by heat exchanger G (using a cooling medium supplied from E and returned via F) prior to addition to the tank (K) where it is contacted with the water or other low viscosity, low boiling liquid (B). The flow of the cooling medium may be adjusted (up or down using valve D3) to reach the desired temperature based on feedback from a temperature meter (TIC; H).

Further, the material in the tank (K) may be recycled back into the tank (K) by pump (M). The return flow into the tank (K) may pass a blender (L) and a viscosity meter (I), and may continue to be recycled until a desired viscosity is reached, at which point the material in the tank (K) may be passed to storage or loading (J) for transfer.

As with the embodiment shown in FIG. 1, instrumentation and controls can ensure that all stream flows are metered and added in appropriate amounts to reach a target blend composition. For example, the control system may adjust the flow rate of B based on the flow rate of A and the desired concentration of B in the blend, and recycling into the tank (K) based on the viscosity readings (I). The setup allows the ratio to be changed to produce blends of different compositions. Additional valves (n) may be included which may control flow of the various feed streams throughout the blending station either automatically or manually.

Example 3

Figure 3:
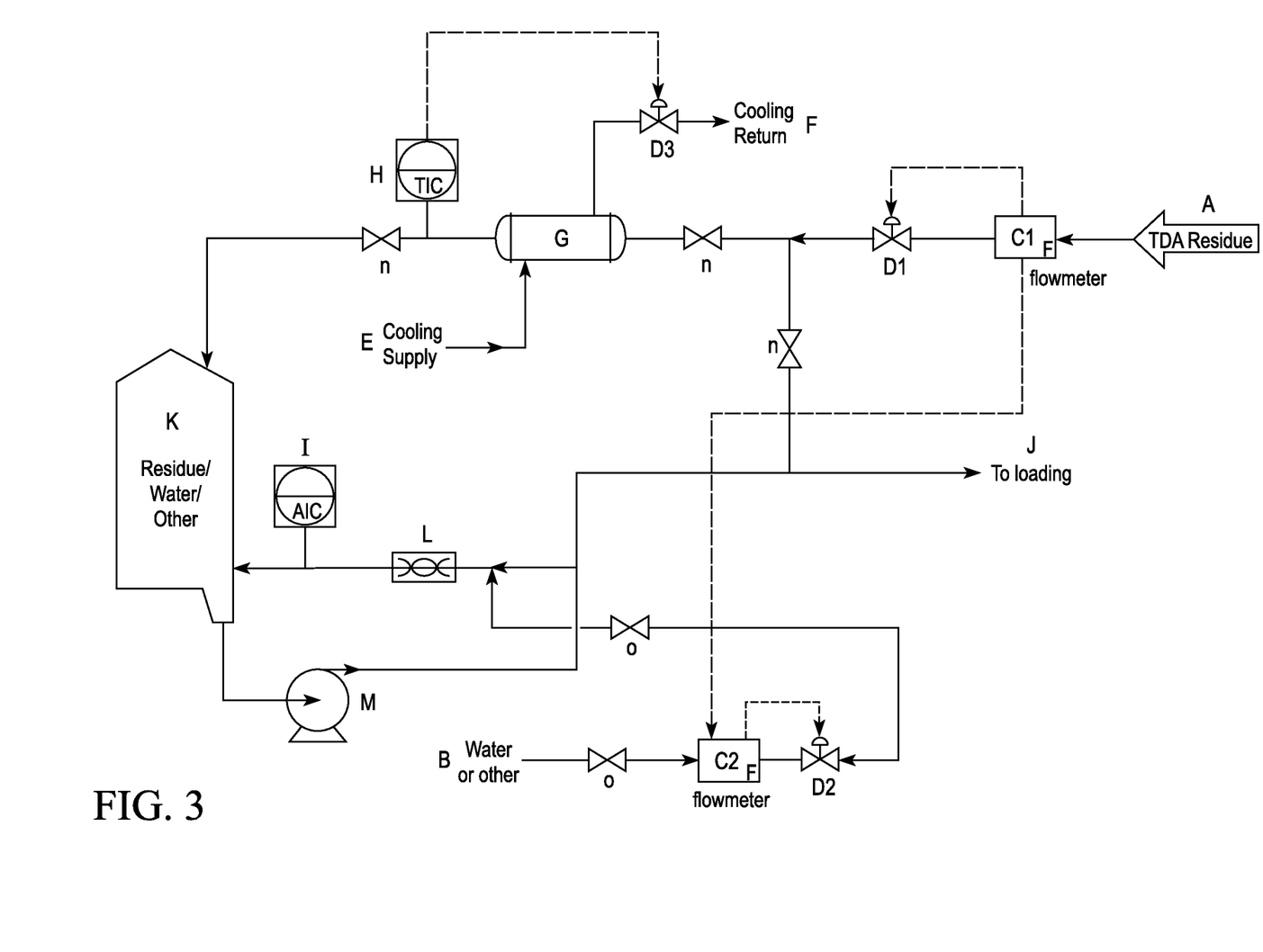
FIG. 3 is a schematic diagram illustrating yet another embodiment of a process control for a process of stabilizing toluenediamine residue compositions according to the present invention.

Shown in FIG. 3 is a schematic diagram for another embodiment of a process control which may be used to practice the process of the present invention. Reference letters in FIG. 3 are the same as those shown in FIG. 2. Additional flow control in this embodiment may be enabled using additional valves (o) which may control flow of the various feed streams throughout the blending station either automatically or manually.

Example 4

Figure 4:
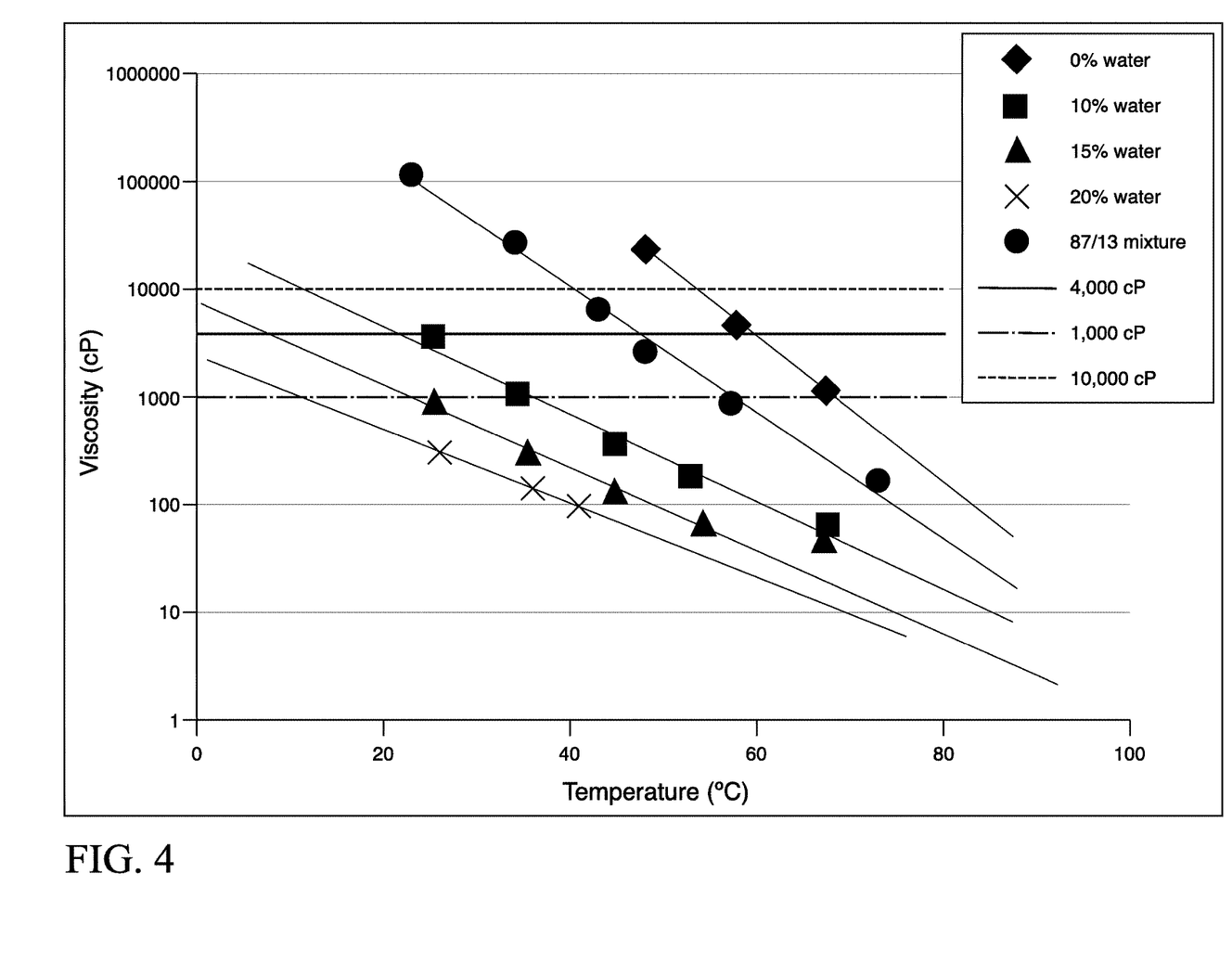
FIG. 4 is a viscosity diagram for various toluenediamine residue composition blends with water plotted as a function of temperature.

Shown in FIG. 4 is a graph of the viscosity as a function of temperature for a series of toluenediamine residue composition—water blends (viscosity plotted on a log$_{10}$ scale; data used for the plot in FIG. 4 is shown in Table 1).

A volume of process water (at 40° C.) was added to a toluenediamine residue composition (at a temperature just below 100° C.) to form various blends—10% by weight water ("10% water"), 15% by weight water ("15% water"), and 20% by weight water ("20% water"), each based on the total weight of the toluenediamine residue composition and the water in the blend). Also tested was a toluenediamine residue composition without added water ("0% water"), and a blend of 87% by weight toluenediamine residue composition and 13% by weight low boiling substances ("87/13 mixture").

A Brookfield DV-1™ Prime with a small cell adapter was used for measurements of the viscosity at various temperatures. The viscometer is calibrated annually by Brookfield and routinely checked using Cannon Viscosity Standards (a range of standard oil viscosities tested at the same temperature, 25° C. and/or 80° C.). A Fluke 1524 Reference Thermometer (calibrated annually) with a Fluke Model 5622 Fast Response Platinum Resistance Thermometer (purchased calibrated and are sent back in for calibration on an annual basis) was used for all temperature measurements. Temperature of the sample cell was measured directly.

Measurements were made using the following protocol: (1.) Load the sample cell with 10-13 mL of sample for use with spindles #18 or #31; (2.) Submerge the thermometer into the sample and begin measuring the temperature; (3.) Wait until the temperature stabilizes to the desired temperature and then remove the thermometer; (4.) Turn on the viscometer to the desired rotation speed (i.e., rpm, the goal being to have the % torque value >50%); (5.) If >50% torque cannot be achieved, change to a larger spindle, such as #18; and (6.) Record the viscosity. Results are set forth in Table 1.

TABLE 1

| 0% water | | 10% water | | 15% water | | 20% water | | 87/13 mixture | |
|---|---|---|---|---|---|---|---|---|---|
| T (° C.) | Viscosity cP | T (° C.) | Viscosity cP | T (° C.) | Viscosity cP | T (° C.) | Viscosity cP | T (° C.) | Viscosity cP |
| — | — | 25.4 | 3659 | 25.5 | 898 | 26.2 | 310.7 | 23 | 120000 |
| — | — | 34.3 | 1092 | 35.5 | 296.9 | 36 | 139.2 | 34 | 28074 |
| 48.2 | 24055 | 44.7 | 364.7 | 44.9 | 134 | 41 | 97.2 | 43 | 6599 |
| 57.8 | 4700 | 52.9 | 179.4 | 54.3 | 68 | — | — | 48 | 2700 |
| 67.4 | 1196 | 67.5 | 66.8 | 67.2 | 46.8 | — | — | 57 | 884 |
| — | — | — | — | — | — | — | — | 73 | 169 |

The line at 10,000 cP (10,000 mPa·s) in the graph of FIG. 4 demonstrates that addition of 10% by weight, 15% by weight or 20% by weight water to the toluenediamine residue composition provided a blend having a viscosity of 10,000 cP or less at temperatures of 20° C. or greater. The line at 4,000 cP (4,000 mPa·s) demonstrates that addition of 10% by weight water to the toluenediamine residue composition provided a blend having a viscosity of 4,000 cP or less at temperatures of 24° C. or greater, while addition of 15% by weight or 20% by weight water to the toluenediamine residue composition provided a blend having a viscosity of 4,000 cP or less at all temperatures measured, specifically at all temperatures of 20° C. or greater. The line at 1,000 cP (1,000 mPa·s) in the graph of FIG. 4 demonstrates that addition of 10% by weight water to the toluenediamine residue composition provided a blend having a viscosity of 1,000 cP or less at temperatures of 33° C. or greater; addition of 15% by weight water to the toluenediamine residue composition provided a blend having a viscosity of 1,000 cP or less at temperatures of 24° C. or greater; and addition of 20% by weight water to the toluenediamine residue composition provided a blend having a viscosity of 1,000 cP or less at all temperatures measured, specifically at all temperatures of 20° C. or greater.

Example 5

Further experiments were done to measure the stability of a toluenediamine residue composition/water blend over time. A blend of 80% by weight toluenediamine residue composition and 20% by weight water was made and a portion of the blends was stored at 25° C. and another portion of the blend was stored at 40° C. The blend was poured into a 3 liter vessel (one half full) and mixed at maximal mixing speed for 1 minute, after which the mixer was turned off. The vessel was maintained at temperature using an electric oil bath set to the desired temperature and a condenser with cooling water was used to keep water from evaporating from the vessel over the course of the time of the experiment. Samples (12 ml) were taken from the top and bottom of the vessel and viscosities measurements were periodically performed (at 25° C.) in the manner indicated above in Example 4. Results are in Table 2.

TABLE 2

| Blend with 20% by weight water stored at 40° C. Day/time | | | | | | |
|---|---|---|---|---|---|---|
| | Day 1 - 15:30 | Day 2 - 15:00 | Day 4 - 10:00 | Day 7 - 14:43 | Day 9 - 15:09 | Day 16 - 7:45 |
| Viscosity top cP | — | 429 | 439 | 480 | 450 | 445 |
| Viscosity bottom cP | — | 419 | 445 | 455 | 448 | 440 |

| Blend with 20% by weight water stored at 25° C. Day/time | | | | |
|---|---|---|---|---|
| | Day 1 - 5:02 | Day 2 - 11:00 | Day 3 - 9:30 | Day 4 - 11:00 |
| Viscosity top cP | 454 | 463 | 457 | 300‡ |
| Viscosity bottom cP | 454 | 454 | 509 | 416 |

‡Crystal formation at top of vessel (66 hour time point).

As shown in Table 2, the blend stored at 40° C. remained stable over the full course of the 16 day test, and may have remained stable for much longer. No significant change in the viscosity at the top or bottom of the vessel was registered, and no crystal formation was observed. The blend that was stored at 25° C. did show an increase in the viscosity at the bottom of the vessel relative to the top of the vessel over time, and crystal formation at the top of the vessel was observed after 66 hours. Thus, the 20% by weight water blend showed no signs of phase separation for 66 hours at 25° C. and over 2 weeks at 40° C.

Example 6

A mixture of 87% by weight toluenediamine residue composition and 13% by weight low boiling substances ("87/13 mixture") was made to test whether addition of the low boiling substances would stabilize the toluenediamine residue composition (i.e., lower the viscosity at a temperature of 50° C. or less). This mixture was also blended with various amounts of water (as indicated in Table 3 in which the % by weight water is based on the total weight of the 87/13 mixture and water in the blend) to test the ability of water to further stabilize the mixture. Results are in Table 3.

TABLE 3

| % by weight | Viscosity (cP) | |
|---|---|---|
| water | 23° C. | 48° C. |
| 0 | 120000 | 2700 |
| 6 | 8614 | 357 |
| 7 | 5339 | 239 |
| 8 | 3533 | 215 |
| 9 | 2869 | 165 |
| 10 | 1968 | 137 |
| 11 | 1659 | 120 |

Figure 5:
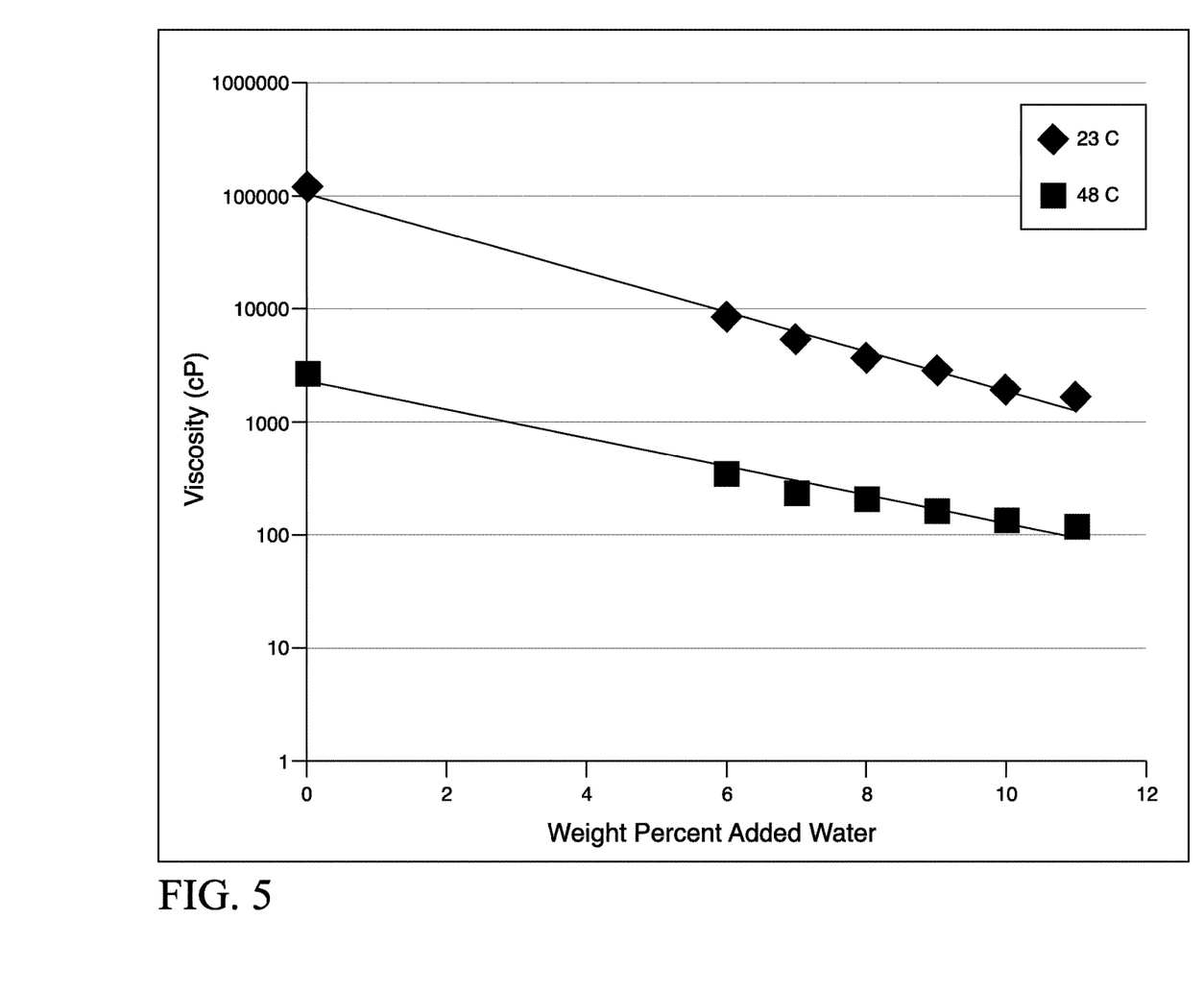
FIG. 5 is a viscosity diagram at two different temperatures for a mixture of 87% by weight of a toluenediamine residue composition with 13% by weight of low boiling substances plotted as a function of added water, wherein the percent added water is based on the total weight percent of the blend (toluenediamine residue composition, low boiling substances, and water).

Shown in FIG. 5 is a graph of the viscosity of the 87/13 mixture as a function of added water at 23° C. and 48° C. (viscosity plotted on a $\log_{10}$ scale; data used for the plot in FIG. 5 is shown in Table 3). More specifically, 13% by weight of low boiling substances was added to 87% by weight of a toluenediamine residue composition as described above to form the 87/13 mixture. Water was then added to this 87/13 mixture (in various amounts ranging from 6 to 11% by weight water based on the total weight of the 87/13 mixture and the water in the blend), and the viscosity was measured at 23° C. or 48° C.) in the manner indicated above in Example 4.

The data in the graph of FIG. 5 demonstrate that addition of 13% by weight of the low boiling substances stabilized the toluenediamine residue composition (all viscosity measurements were below 4,000 cP (4,000 mPa·s)) for temperatures of 48° C. or greater. The addition of water further reduced the viscosity of the mixture, so that with as little as 6% by weight water the blend has a viscosity below 10,000 cP (1,000 mPa·s) at 23° C.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:
1. A process for stabilizing toluenediamine residues, the process comprising:
    adding a low viscosity, low boiling liquid to a toluenediamine residue composition to form a blend,
    wherein the blend comprises 5 to 30% by weight of the low viscosity, low boiling liquid, based on the total weight of the blend, and
    wherein the blend has a viscosity of 10,000 cP or less throughout the temperature range of 40° C. to 95° C., and
    wherein the toluenediamine residue composition comprises:
        (a) 25 to 60% by weight of toluenediamine residue and 40 to 75% by weight of meta-toluenediamine isomer, based on the total weight of the toluene diamine residue and the meta-toluenediamine isomer in the composition;
        (b) 25 to 60% by weight of toluenediamine residue and 40 to 75% by weight of ortho-toluenediamine isomer, based on the total weight of the toluenediamine residue and the ortho-toluenediamine isomer in the composition; or
        (c) 25 to 60% by weight of toluenediamine residue and 40 to 75% by weight of a mixture of meta-toluenediamine and ortho-toluenediamine isomers, based on the total weight of the toluenediamine residue and the mixture of meta-toluenediamine and ortho-toluenediamine isomers in the composition.
2. The process of claim 1, further comprising:
    continuously monitoring the viscosity of the blend during addition of the low viscosity, low boiling liquid; and
    controlling an amount of toluenediamine residue composition and/or controlling an amount of the low viscosity, low boiling liquid added based on the viscosity of the blend.
3. The process of claim 2, further comprising passing the blend through a heat exchanger to bring the temperature of the blend to a target temperature range for use as a liquid fuel.
4. The process of claim 1, wherein the blend has a viscosity of 4,000 cP or less throughout the temperature range of 40° C. to 95° C.
5. The process of claim 1, wherein the blend has a viscosity of 2,000 cP or less throughout the temperature range of 40° C. to 95° C.
6. The process of claim 1, wherein the low viscosity, low boiling liquid comprises water.
7. The process of claim 6, wherein the water comprises water recovered during crude toluenediamine purification to isolate meta-toluenediamine.
8. The process of claim 6, wherein the amount of water in the blend is 10 to 20% by weight, based on the total weight of the blend.
9. The process of claim 1, wherein the toluenediamine residue composition comprises a mixture of toluenediamine isomers and toluenediamine residues, wherein the toluenediamine residues comprise compounds formed during toluenediamine synthesis that have a higher boiling point than the 2,6 TDA isomer.
10. A blended composition comprising:
    70 to 95% by weight of a toluenediamine residue composition; and
    5 to 30% by weight of a low viscosity, low boiling liquid, wherein the weight percents are based on the total weight of the composition,
    wherein the blended composition has a viscosity of 10,000 cP or less throughout the temperature range of 40° C. to 95° C., and
    wherein the toluenediamine residue composition comprises:

(a) 25 to 60% by weight of toluenediamine residue and 40 to 75% by weight of meta-toluenediamine isomer, based on the total weight of the toluene diamine residue and the meta-toluenediamine isomer in the composition;

(b) 25 to 60% by weight of toluenediamine residue and 40 to 75% by weight of ortho-toluenediamine isomer, based on the total weight of the toluenediamine residue and the ortho-toluenediamine isomer in the composition; or (c) 25 to 60% by weight of toluenediamine residue and 40 to 75% by weight of a mixture of meta-toluenediamine and ortho-toluenediamine isomers, based on the total weight of the toluenediamine residue and the mixture of meta-toluenediamine and ortho-toluenediamine isomers in the composition.

11. The blended composition of claim 10, wherein the blended composition has a viscosity of 4,000 cP or less throughout the temperature range of 40° C. to 95° C.

12. The blended composition of claim 10, wherein the blended composition has a viscosity of 2,000 cP throughout the temperature range of 40° C. to 95° C.

13. The blended composition of claim 10, wherein the toluenediamine residue composition comprises a mixture of toluenediamine isomers and toluenediamine residues, wherein the toluenediamine residues comprise compounds formed during toluenediamine synthesis that have a higher boiling point than the 2,6-TDA isomer.

14. The blended composition of claim 10, wherein the low viscosity, low boiling liquid comprises water.

15. The blended composition of claim 14, comprising 80 to 90% by weight of the toluenediamine residue composition and 10 to 20% by weight water.

16. A method of using a toluenediamine residue composition, the method comprising:

(a) feeding a blend comprising the toluenediamine residue composition to a fuel burning apparatus, wherein the blend comprises 70 to 95% by weight of the toluenediamine residue composition and 5 to 30% by weight of a low viscosity, low boiling liquid, wherein the weight percents are based on the total weight of the blend; and (b) burning the blend in the fuel burning apparatus, wherein the blend has a viscosity of 10,000 cP or less throughout the temperature range of 40° C. to 95° C., and wherein the toluenediamine residue composition comprises:

(i) 25 to 60% by weight of toluenediamine residue and 40 to 75% by weight of meta-toluenediamine isomer, based on the total weight of the toluene diamine residue and the meta-toluenediamine isomer in the composition;

(ii) 25 to 60% by weight of toluenediamine residue and 40 to 75% by weight of ortho-toluenediamine isomer, based on the total weight of the toluenediamine residue and the ortho-toluenediamine isomer in the composition; or (iii) 25 to 60% by weight of toluenediamine residue and 40 to 75% by weight of a mixture of meta-toluenediamine and ortho-toluenediamine isomers, based on the total weight of the toluenediamine residue and the mixture of meta-toluenediamine and ortho-toluenediamine isomers in the composition.

17. The method of claim 16, wherein the toluenediamine residue composition comprises a mixture of toluenediamine isomers and toluenediamine residues, wherein the toluenediamine residues comprise compounds formed during toluenediamine synthesis that have a higher boiling point than the 2,6-TDA residue.

18. The method of claim 16, wherein the blend comprises 80 to 90% by weight of the toluenediamine residue composition and 10 to 20% by weight of the low viscosity, low boiling liquid, wherein the low viscosity, low boiling liquid comprises water and the weight percents are based on the total weight of the blend.

19. The method of claim 16, wherein the blend has a viscosity of 4,000 cP or less throughout the temperature range of 40° C. to 95° C.

20. The method of claim 16, wherein the fuel burning apparatus comprises a boiler, a rotary kiln incinerator, a liquid injection kiln, a fluidized bed kiln, a cement kiln, or a metals forging furnace.

21. The method of claim 20, wherein the fuel burning apparatus is a cement kiln.

* * * * *